(12) United States Patent
Cailleteau (10) Patent No.: US 10,413,138 B2
(45) Date of Patent: Sep. 17, 2019

(54) FLEXIBLE BAG WITH OPENING SLEEVE WITH SPOUT

(71) Applicant: Swiss Safe Collect SA, Neuchâtel (CH)

(72) Inventor: Benoît Cailleteau, Marseilles (FR)

(73) Assignee: SWISS SAFE COLLECT SA, Neuchatel (CH)

( * ) Notice: Subject to any disclaimer, the term of this patent is extended or adjusted under 35 U.S.C. 154(b) by 309 days.

(21) Appl. No.: 14/890,915

(22) PCT Filed: May 13, 2014

(86) PCT No.: PCT/EP2014/059724
§ 371 (c)(1),
(2) Date: Nov. 13, 2015

(87) PCT Pub. No.: WO2014/184174
PCT Pub. Date: Nov. 20, 2014

(65) Prior Publication Data
US 2016/0088983 A1 Mar. 31, 2016

(30) Foreign Application Priority Data

May 13, 2013 (FR) .................................... 13 54249

(51) Int. Cl.
*A47K 11/12* (2006.01)
*A61G 9/00* (2006.01)
(Continued)

(52) U.S. Cl.
CPC .............. *A47K 11/12* (2013.01); *A61F 5/451* (2013.01); *A61G 9/006* (2013.01); *B65D 33/007* (2013.01); *A61G 2200/12* (2013.01)

(58) Field of Classification Search
CPC ......... A47K 11/12; A61F 5/453; A61F 5/455; A61F 5/4556
(Continued)

(56) References Cited

U.S. PATENT DOCUMENTS 2,172,930 A * 9/1939 Bensel ................... B65D 5/062
229/137
3,334,797 A * 8/1967 Latham ................ B65D 17/165
220/268
(Continued)

FOREIGN PATENT DOCUMENTS

EP 0847742 A1 6/1998
FR 2735358 A1 12/1996
(Continued)

OTHER PUBLICATIONS

Notice of Reasons for Rejection dated Apr. 3, 2018 in corresponding JP Application No. 2016-513329, 10 pages.
(Continued)

*Primary Examiner* — Erin Deery
*Assistant Examiner* — Nicholas A Ros
(74) *Attorney, Agent, or Firm* — MH2 Technology Law Group, LLP (57) ABSTRACT

The pouch (10) comprises a flexible bag (12) having an opening (12A) with its edge fastened to two opposite walls (20A, 20B) of a reinforcing collar (18) projecting out from the bag, the pouch being suitable for adopting a flat configuration in which the collar is folded along a main fold line (17) connecting together its walls so that said walls are situated one against the other, and a utilization configuration in which the walls form a channel holding the opening open. The main fold line (17) presents an end portion (17A) opposite from the opening that projects laterally outwards, such that in the utilization configuration, the collar presents a nose defined by said end portion.

14 Claims, 4 Drawing Sheets

(51) Int. Cl.
*B65D 33/00* (2006.01)
*A61F 5/451* (2006.01)

(58) Field of Classification Search
USPC .............. 383/119, 33, 61.5, 64, 906, 96, 36;
4/144.1–144.4, 307, 484
See application file for complete search history.

(56) References Cited

U.S. PATENT DOCUMENTS

| | | | |
|---|---|---|---|
| 3,597,770 A * | 8/1971 | Jacuzzi | A61G 9/006 4/144.2 |
| 5,044,774 A * | 9/1991 | Bullard | B65D 33/007 383/33 |
| 5,387,205 A * | 2/1995 | Cummins | A61B 10/007 4/144.3 |
| 5,946,738 A * | 9/1999 | Cailleteau | A61F 5/4404 4/144.1 |
| 6,345,911 B1 * | 2/2002 | Young | A61J 19/00 383/104 |
| 9,539,158 B2 * | 1/2017 | Cassidy | A61G 9/006 |
| 2010/0230407 A1 * | 9/2010 | Savage | B65D 33/30 220/9.4 |
| 2010/0318044 A1 * | 12/2010 | Takayama | A61F 5/451 604/317 |
| 2012/0222208 A1 * | 9/2012 | Jacobson | A61F 5/4556 4/484 |

FOREIGN PATENT DOCUMENTS

| | | | |
|---|---|---|---|
| FR | 2898269 A1 | 9/2007 | |
| JP | 2003125975 A | 5/2003 | |
| JP | 2010-284272 A | 12/2010 | |

OTHER PUBLICATIONS

Russian Office Action dated Apr. 2, 2018 for Russian Application No. 2015153415/12(082382), 11 pages.

* cited by examiner

FLEXIBLE BAG WITH OPENING SLEEVE WITH SPOUT

The present invention relates to a pouch comprising a flexible bag having an opening whose edge is fastened to two opposite walls of a reinforcing collar projecting out from the bag, the pouch being able to adopt a flat configuration in which the collar is folded along a main fold line connecting together its walls so that said walls are situated one against the other, and a utilization configuration in which the walls form a channel holding the opening open.

Pouches of this type are known, e.g. from European patent No. 0 847 742. They are used for receiving substances generally in liquid form, in particular waste of human or animal origin such as urine. Such pouches are stored in their flat configuration. In order for them to be used, the collar is manipulated so as to cause its walls to form a channel that holds the opening open, thus putting the pouch into its utilization configuration, in which the waste can be poured into the inside of the pouch. Once the waste has been inserted, for the pouch to return to its flat configuration, it suffices to release the collar.

Such pouches are commonly made of thin sheets of plastics or other material, possibly transparent material, and presenting a desired degree of flexibility. For opening purposes, the manipulation of the collar consists in deforming its walls so as to force them to adopt a convex shape (as seen from outside the pouch) in which they form therebetween the channel that holds the opening open.

European patent application No. 0 847 742 is concerned with ensuring that the manipulation of the collar for shaping it into a channel causes the walls of the bag to space apart not only at the edges of the opening of the bag, but also downstream from that opening so as to avoid the substance that is being inserted into the pouch having any tendency to reflux. For that purpose, the collar has internal spacer tabs. This gives great freedom in selecting the material from which to make the bag of the pouch. The invention of the above-specified European patent application makes it possible to ensure that the sheets of the bag move apart, even if they are very flexible, and even if they initially present a tendency to remain lightly stuck together.

A problem that arises in preparing a pouch of the above-specified type is that of ensuring that substances (and in particular waste such as urine) are conveyed effectively to the inside of the bag. When the pouch is used as a male urinary pouch, that does not normally raise any particular difficulty once the user's penis is inserted through the opening (in the channel formed by the collar) over a sufficient length. Likewise, in all applications to collecting waste where the waste is inserted into the pouch from a projecting member or endpiece that can be inserted into the pouch through the opening over a length that is sufficient, conveying substances to the inside of the pouch generally does not present any difficulty.

In contrast, difficulties arise when it is desired to use pouches for other applications in which the member from which the substances flow is not of a type that can be inserted into the channel formed by the collar, or that cannot be inserted therein over a sufficient length. This applies for example when the pouches are used as female urinary pouches. Under such circumstances, the substances, e.g. urine, are inserted into the pouch from the end of the collar that projects outside the bag.

The Applicant has found that, when the free edge of the collar presents the shape described in European patent application No. 0 847 742, the guidance of substances from that free edge can be insufficient. This applies in particular when the pouch is used as a female urinal.

Patent application FR 2 735 358 relates specifically to a female urinal in which the free edge is supposed to present a shape that matches female anatomy. Nevertheless, that urinal is entirely rigid. Unlike the pouch of the present invention, it is therefore not suitable for being stored in limited space.

Patent application FR 2 898 269 relates to a pouch constituting a female urinary pouch that has a collar that is said to be ergonomic, and that is supposed to present a shape that matches female anatomy. Nevertheless, that collar is itself rigid and therefore cannot be flattened, which likewise penalizes storage space.

The invention seeks to remedy the above-mentioned drawbacks by proposing a pouch that can adopt a flat configuration and that presents a collar with a shape that facilitates guiding substances that are being inserted into the pouch towards the bottom of the pouch, while limiting any risk of leakage, in particular when the pouch is used as a female urinary pouch.

This object is achieved by the fact that the main fold line presents an end portion opposite from the opening that projects laterally outwards, such that in the utilization configuration, the collar presents a nose defined by said end portion.

By means of these provisions, when the collar is manipulated to pass into its utilization configuration, the nose forms naturally. This nose enhances guidance of substances towards the inside of the pouch. In particular, when the pouch is used as a female urinal, the nose may be placed against the posterior portion of the vulva, thus limiting any risk of urine leaking between the female anatomy and the pouch.

The pouch of the invention has numerous applications. Because of the presence of the nose, substances are conveyed better along the channel into the pouch, which is particularly useful when, in general manner, the substances flow from members that cannot be inserted into the pouch. It is also useful when substances flow from members that can be inserted into the pouch, since the invention makes it possible to avoid leaks without it being necessary to take particular care about the depth up to which the members in question are inserted into the pouch.

Advantageously, the main fold line presents a concave side facing towards the outside of the collar.

When passing the collar from its flat configuration to its utilization configuration, this concave side produces a vaulting effect that forces the nose to take up its shape naturally, by enhancing "unfolding" along the fold line.

Advantageously, each of the walls of the collar presents a secondary fold line that connects the main fold line to the free edge of the collar opposite from the opening, and that, in the utilization configuration, forms a boundary between the nose and a remaining portion of the collar.

While the collar is passing from its flat configuration to its utilization configuration, the walls of the collar tend to become indented along the secondary fold lines, thereby further enhancing the shaping of the nose.

Advantageously, the secondary fold lines are symmetrical relative to the main fold line.

The nose is thus itself shaped symmetrically.

Advantageously, the secondary fold lines are curved, with concave sides facing towards the main fold line.

This enhances the shaping of the nose so that it projects laterally outwards.

Advantageously, the extent to which the collar projects from the opening varies across the width of the collar, between a minimum height measured in the vicinity of the main fold line and a maximum height measured in the vicinity of the lateral end of the collar opposite from the main fold line.

This variation in height is particularly advantageous when the pouch is used as a female urinary pouch, since it makes it easier to press the free edge of the collar against the vulva of the woman using the pouch, with the portion of lowest height that includes the nose being arranged against the posterior portion of the vulva.

Advantageously, the first wall of the collar presents a first longitudinal end strip projecting laterally relative to the edge of the opening, while the second wall presents a sliding edge suitable for sliding against the inside face of said first longitudinal strip while the pouch is passing from its flat configuration to its utilization configuration.

Thus, when pressure is applied to the longitudinal edges of the collar so as to move them towards each other, the first wall of the collar is certainly deformed into a convex shape because the first longitudinal end edge projects laterally relative to the edges of the opening. With this first wall being made convex, the sliding edge of the second wall has no other choice than to slide against the inside face of the first longitudinal strip, which inside face is thus concave. Consequently, the second wall moves away from the first wall, such that the two walls form between them the desired channel for holding the opening open. Furthermore, the sliding contact between the sliding edge and the second wall provides a degree of sealing preventing the waste that is being inserted into the pouch from leaking via the edge of the channel that has the sliding edge and the first desired longitudinal strip.

In particular, the collar may be made by molding a plastics material, e.g. by injection molding, so as to be in the form of a single piece that presents both of the walls that are connected together by the main fold line. It is also possible to make the collar from two flanks that are cut out flat with each of them forming a respective one of the walls, the flanks then being connected together (by welding or the like) along the main fold line.

With the present invention, a large degree of freedom is left as to the shape of the free edge of the collar opposite from the opening. This edge may be rectilinear, e.g. when the pouch is used as a male urinal. In other applications, e.g. when the pouch is used as a female urinal, it is possible for it to have some other shape, as mentioned above.

Advantageously, the pouch includes means for holding the walls of the collar in their channel-forming shape.

For example, the collar presents two holder tongues carried respectively by the first and second walls of the collar, on the side opposite from the opening of the pouch and in a zone that is remote from the main fold line, the holder tongues overlapping at least in part in the utilization position.

These holder tongues thus form a grip zone enabling the collar, when shaped into a channel, to be gripped and held in its channel shape.

Provision may also be made for two portions of the collar, that are to move into overlap when the walls of the collar are in their channel-forming shape, to present respectively a hole and a lug suitable for being engaged in said hole.

These two portions that are to move into overlap are advantageously situated in respective zones of the first and second walls of the collar that are remote from the main fold line.

The invention can be well understood and its advantages appear better on reading the following detailed description of an embodiment given by way of non-limiting example. The description refers to the accompanying drawings, in which.

Figure 1:
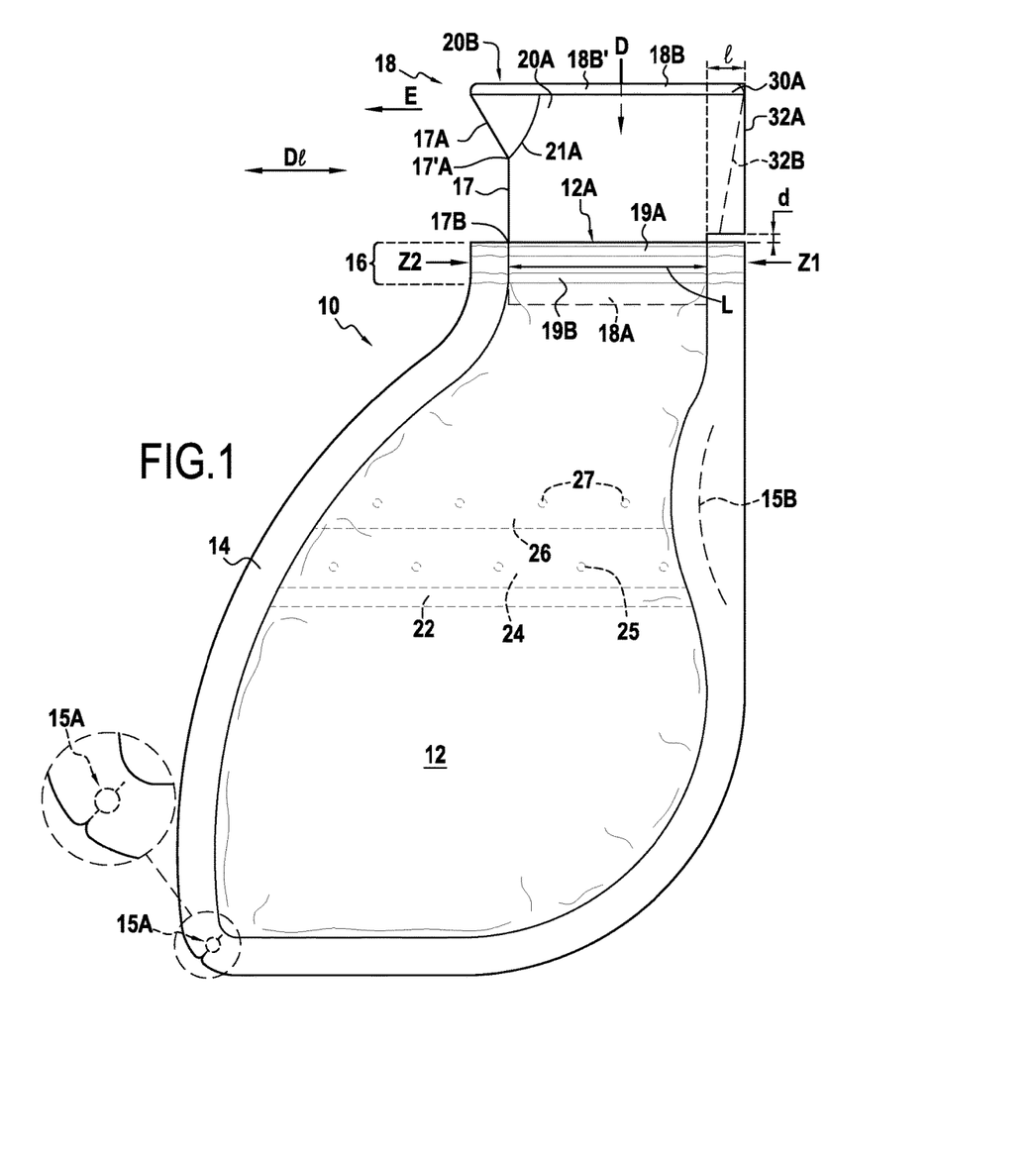
FIG. 1 is a plan view of a pouch in accordance with the invention, in its flat configuration.

The pouch 10 shown in FIG. 1 comprises a flexible bag 12. In particular, the bag is made from two thin sheets of plastics material that are cut out in suitable manner and welded together over almost all of the outline by means of a weld line 14. The bag 12 has an opening 12A constituted by an interruption in the weld line 14 so as to enable the inside space of the bag to communicate with the outside.

In the example shown, this opening is arranged at the free end of a neck portion 16 presented by the bag, where the width of the bag is reduced.

The bag comprises a reinforcing collar 18 that is fastened through the opening 12A and projects to the outside of the bag.

Specifically, the collar comprises not only its main collar portion proper, which portion projects outside the opening 12A, but also an internal portion 18A that is inserted into the opening so as to extend across the entire width L of the opening.

By way of example, the sheets that form the bag are made of flexible plastics material, while the collar is made of more rigid plastics material. Thus, in order to fasten the collar to the bag, it suffices to weld or adhesively bond the sheets of the bag to the walls of the collar. Thus, FIG. 1 shows two weld lines referenced respectively 19A and 19B that extend transversely relative to the direction D in which waste is inserted into the pouch, with the front wall 20A of the collar, as can be seen in FIG. 1, being welded along these lines to the corresponding sheet of the bag. Naturally, the rear portion 20B of the collar is welded in the same manner to the opposite sheet of the pouch.

It can also be seen in FIG. 1 that, in a region opposite from the opening, the line of welding 14 presents a line of weakening 15A, e.g. made by microperforations in the form of dots. This weakening extends only over the line of welding without reaching the inside space of the bag. When the pouch is full of waste, the waste can thus be emptied by tearing the bag along the line of weakness 15A, with sufficient force to ensure that the resulting tear extends into the inside space of the bag.

Furthermore, on one of these sides adjacent to the opening, the weld line 14 presents another line of weakening 15B that may also be implemented in the form of discontinuous perforations. This line is at a distance from the inside space of the bag and it extends in such a direction that if it is torn, the tear cannot propagate to the inside of the bag. Thus, when the pouch is full and it is desired to store it before emptying it, the line 15B can be torn in order to provide a slot enabling the pouch to be attached to a hook or the like.

It can also be seen in FIG. 1 that the pouch presents a safety valve of the type described in European patent application No. 0 847 742. Thus, this valve is constituted by a plurality of internal sheets arranged against each of the walls of the pouch. In the example shown, for each of the two walls of the pouch, the valve comprises a first pair of sheets 22 extending from the opening 12A to a middle region of the pouch, a second pair of sheets 24 extending inside the sheets of the first pair 22, and a third pair of sheets 26 extending inside the pair of sheets 24, the sheets 26 being shorter than the sheets 24, which themselves are shorter than the sheets 22. These sheets extend over the entire width of the pouch in the region where they are located, and they are thus welded to one another and to the walls of the bag by the weld line 14. Furthermore, the sheets of the pair 24 are welded together by spot welds 25 and the sheets of the pairs 26 and 24 are welded together by spot welds 27 that are offset relative to the spot welds 25. These various pairs of sheets suitably welded together thus constitute an anti-reflux valve that prevents reflux of the waste situated in the pouch while it is being handled after being used.

It can be seen that the line of weakening 15B is located in a region of the weld line where some or all of the various layers of sheets are present, such that this weld is particularly strong, which is appropriate for the above-mentioned attachment.

The invention relates most particularly to the collar 18. As mentioned above, it is welded across the opening with its internal portion 18A extending across the entire width L of the opening 12A. In FIG. 1, which is a side view, the collar 18 is flattened and its front wall 20A, referred to below as its "first" wall, can be seen, while its second wall 20B is hidden by the first wall.

Figure 2:
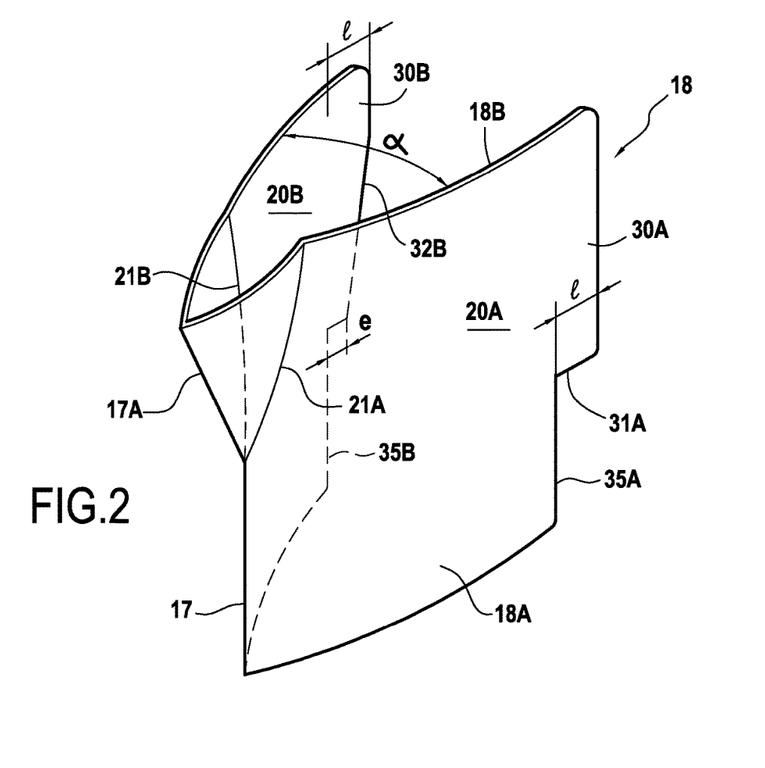
FIG. 2 is a perspective view showing the collar of the pouch of FIG. 1.

With reference also to FIG. 2, it can be understood that the two walls 20A and 20B are connected together by a main fold line 17. It can also be seen that this main fold line 17 presents an end portion 17A (its end opposite from the opening 12A) that projects laterally and outwards. The term "outwards" is used herein to mean the direction represented by arrow E in FIG. 1, going away from the longitudinal edges of the collar opposite from the main fold line 17, it being specified that in the meaning of the present patent application, the longitudinal direction is the direction D for inserting waste into the pouch, which direction is itself defined by the axis of the collar 18.

Figure 4:
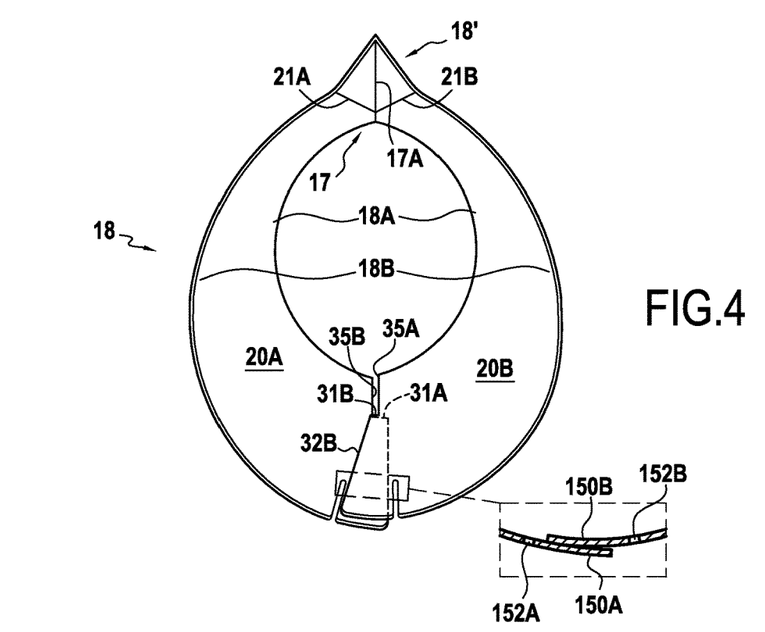
FIG. 4 is a perspective view showing the shape of the collar in the utilization configuration of the pouch of FIG. 1.

It should be observed that the end portion 17A projects laterally outwards both when the pouch is in its flat configuration (as shown in FIG. 1) and when the pouch is in its utilization configuration (as shown in FIG. 4).

FIG. 4 shows the shape of the collar when the pouch is in its utilization configuration, and in this utilization configuration, it can be seen that the projecting portion 17A is shaped to form a nose 18'.

As can be seen in particular in FIGS. 1 and 2, the main fold line 17 presents a concave side facing towards the outside of the collar, i.e. in the direction of arrow E. Specifically, the base 17B of the main fold line 17 is substantially rectilinear and longitudinal in direction, with the fold line has a bend to present the projecting portion 17A, which projecting portion is likewise substantially rectilinear. In the example shown, the bend 17'A forms an angle, and both of the two segments of the fold line that are situated on either side of the bend are rectilinear. Nevertheless, it is entirely possible to provide a bend that is smoother and/or segments that are slightly curved.

In the example shown, each of the walls 20A and 20B of the collar presents a secondary fold line given respective references 21A and 21B. On each wall, the secondary fold line 21A or 21B connects the main fold line 17 to the top edge 18B of the collar 18, i.e. to the free edge of the collar that is opposite from the opening 12A of the pouch.

These secondary fold lines facilitate giving volume to the nose 18' when the collar passes from its flat configuration to its utilization configuration. The secondary fold lines 21A and 21B form boundaries between the nose 18' and the remainder of the collar. When the pouch passes into its utilization configuration, the collar is shaped as a channel and its walls 18A and 18B tend naturally to curve along the secondary fold lines 21A and 21B, with the nose naturally taking up its shape.

As can be seen in particular in FIGS. 2 and 4, the secondary fold lines 21A and 21B are symmetrical about the main fold line 17. Furthermore, in the example shown, the secondary fold lines are curved, with their concave sides facing towards the main fold line. Nevertheless, they could be rectilinear, in general sloping relative to the longitudinal direction, or they could be made up of rectilinear segments.

It can be understood that the nose 18' facilitates the guiding of substances, in particular urine, into the collar and consequently into the pouch. Because of the shape of the main fold line 17 and because of the shape of the secondary fold lines, when present, the nose is formed naturally when the collar is shaped into a channel for using the pouch. It can be seen that the presence of the nose does not in any way prevent the pouch and the collar from adopting a configuration that is entirely flat for storage purposes.

There follows a description of another aspect of the collar 18. It should be observed that the front wall 20A of the collar presents a first longitudinal end strip 30A that projects laterally relative to the edge of the opening 12A. This first longitudinal strip 30A projects a little through a width l relative to the edge of the opening in the lateral direction Dl that is perpendicular to the longitudinal direction D. With reference to FIG. 2, it can be understood that the inside portion 18A of the collar is defined relative to the portion of the collar that projects outside the opening when the collar is in place in the pouch, by means of a step 31A of width l.

On the other side, the second wall 20B of the collar presents a sliding edge 32B that is suitable for sliding against the inside face of the first strip 30A when the pouch passes from its flat configuration to its utilization configuration.

In order to cause the collar to change shape and reach the situation shown in FIG. 4, the user exerts pressure on zones Z1 and Z2 referenced in FIG. 1 that are situated at the base of the collar.

Under the effect of this pressure, which tends to move the opposite longitudinal edges of the collar towards each other, the walls of the collar become curved so as to shape the collar into a channel.

Simultaneously, since the zone Z1 lies under the nose, it takes on the shape of a pouring spout.

More precisely, the walls 20A and 20B of the collar fold along the secondary fold lines 21A and 21B, as described above. The portions of the walls of the collar that are situated between the secondary fold lines 21A and 21B and the main fold line 17 (towards the top of FIG. 4) move apart from each other, while continuing to project laterally outwards, thereby giving the nose 18' the shape of a pouring spout.

The longitudinal strip 30A and the sliding edge 32B make it easier to shape the collar into a channel. Under the effect of pressure on the zones Z1 and Z2, the first wall 20A adopts a convex shape while its longitudinal end strip, which forms a free extension of this first wall, also adopts a convex shape, but with less curvature. The inside face of the first wall 20A exerts a reaction force against the free edge 32B and, because of the particular shape adopted by the first longitudinal strip 30A, the sliding edge has no other choice than to slide over this inside face so as to from the second wall 20B with a convex shape. Thus, the two walls define between them the channel that leads to the opening in the pouch being held in an open situation.

Specifically, the sliding edge 32B is shaped on the edge of a second longitudinal end strip 30B that forms a portion of the second wall of the collar and that projects laterally relative to the edge of the opening. Over at least a segment, the strip 30B projects laterally to a smaller extent than the strip 30A. Specifically, the extent to which the strip 30B projects laterally varies as a result of the sliding edge 32B sloping between the minimum value e of this projection at the step 31B situated at the base of the sliding edge 32B, and the maximum value l at the free edge of the collar.

FIG. 2 shows the collar in the form of a part, with its walls 20A and 20B being connected together by the fold line 17. The collar could be obtained as a single piece, e.g. by injection molding. Under such circumstances, the flare angle α between its two walls may be of the order of 30° to 90°, and preferably about 60°, in order to facilitate unmolding. The fold lines 17, 21A, and 21B are advantageously formed by local reductions in the thickness of the material of the collar.

Figure 3:
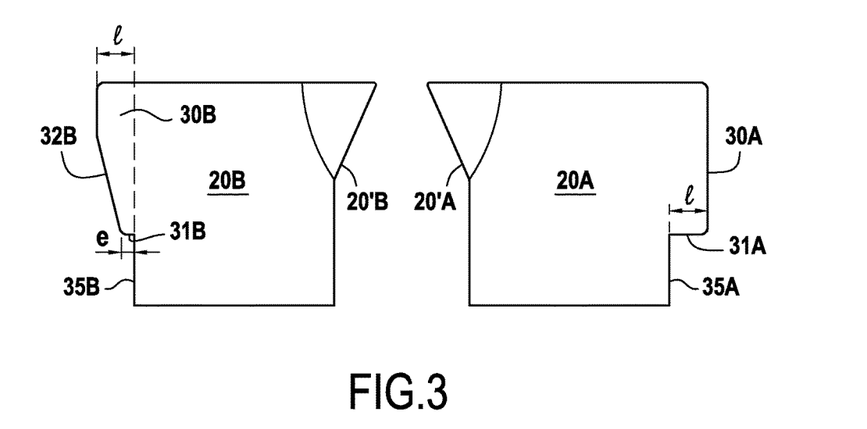
FIG. 3 is a plan view showing the two walls of the collar of FIG. 1, in a variant.

As shown in FIG. 3, it is also possible to provide for making the collar out of two flat parts, i.e. in the form of two distinct flanks respectively forming the walls 20A and 20B, which walls are welded together along their respective edges 20'A and 20'B so that these welded-together edges form the fold lines. The welding is then performed so as to facilitate folding, in particular while avoiding local extra thicknesses.

The edges of the collar opposite from the main fold line 17 are free to move relative to each other. This relates to the entire portion of the collar that projects beyond the opening 12A. Specifically, concerning the internal portion 18A of the collar, it is mentioned above that the width L of this internal portion in the flat configuration corresponds to the width of the opening 12A. Thus, for this internal portion, the edges 35A and 35B are incapable or substantially incapable of moving relative to each other because of the presence of the weld line 14. On the sides of the opening 12A, the weld line 14 may also engage a little with the collar, i.e. on the portion of the main fold line 17 that extends over the internal portion 18A of the collar, and over the above-mentioned edges 35A and 35B.

In the example shown in FIGS. 1 to 4, the extent to which the collar projects away from the opening is substantially constant. Naturally, this does not mean that the top edge 18B of the collar 18 cannot be slightly rounded, should that be necessary. It may thus be chamfered or provided with a rounded bead 18B'.

Figure 5:
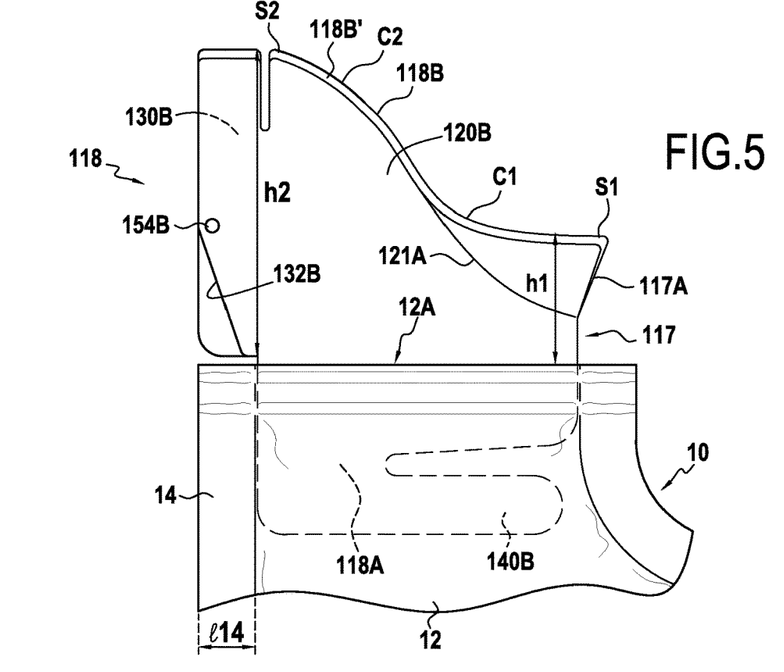
FIG. 5 is a plan view of the portion of a collar close to its opening, in a variant embodiment, that is particularly adapted for use as a female urinal.
Figure 6:
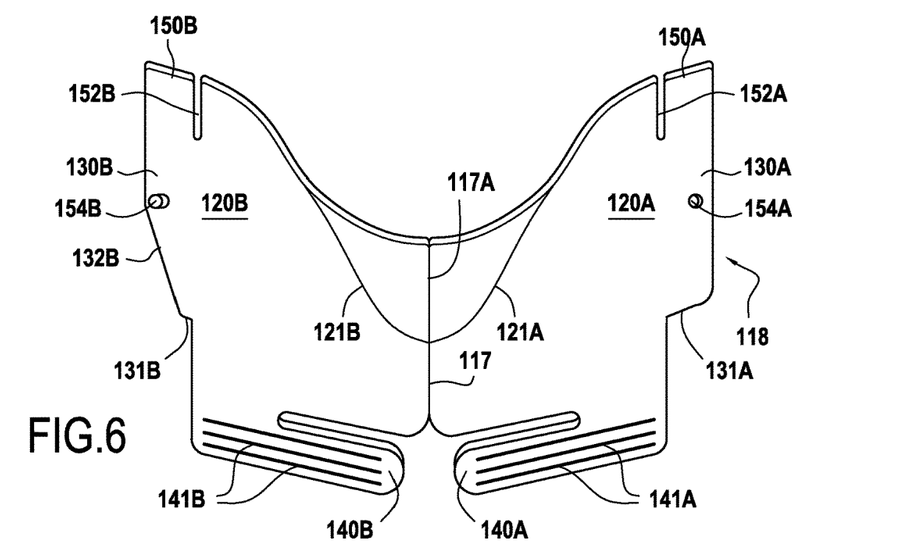
FIG. 6 is a perspective view of the collar of the pouch of FIG. 5.
Figure 7:
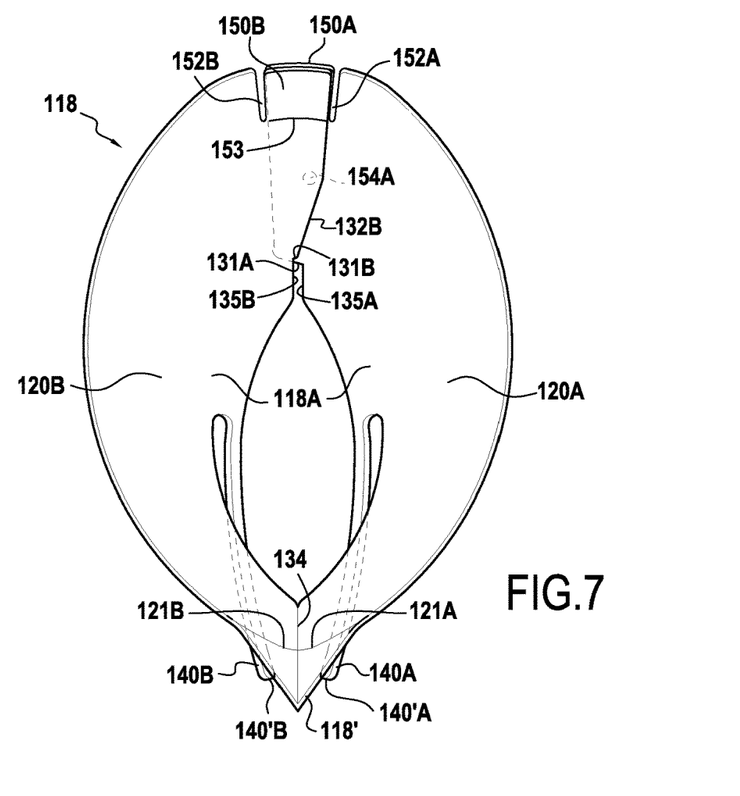
FIG. 7 is a perspective view showing the shape of the collar in the utilization configuration of the pouch of FIG. 5.

With reference to FIGS. 5 to 7, there follows a description of a variant embodiment of the collar. In FIG. 5, only the portion of the pouch that is close to its opening 12A is shown. The collar 118 is analogous to the above-described collar 18, but it differs therefrom in two aspects. Firstly, the free edge 118B of the collar 118 opposite from the opening 12A has a particular shape, and in particular a shape that is adapted for its use as a urinal for women. It can thus be seen that this free edge may have a rounded bead or the like 118B' making it feel more comfortable to the touch. Furthermore, the internal portion 118A of the collar presents spreader tabs that are described below.

The various elements constituting the collar 118 are given the same references as for the collar 18, plus 100. With reference to FIGS. 5 to 7, it can thus be seen that the collar 118 presents a first wall 120A and a second wall 120B that are connected together by a main fold line 117 having a projecting end portion 117A. Each of these walls has a secondary fold line, respectively referenced 121A and 121B.

Furthermore, the first wall 120A has a first longitudinal end strip 130A, while the second wall 120B presents a sliding edge 132B arranged at the edge of a second longitudinal strip 130B. The two longitudinal strips project laterally beyond the opening 12A. The first longitudinal strip 130A is generally situated in line with the weld line 14 and presents a width that corresponds approximately to the width of the weld line.

The second longitudinal strip 130B presents a free terminal portion 130B' of width that is substantially constant, corresponding to the width 114 of the weld line 14. Between the edge of the opening 12A and this terminal portion 130B', the second longitudinal end strip presents the sliding edge 132B that slopes like the sliding edge 32B of the above-described variant in order to slide better against the inside face of the first longitudinal strip 130A. Steps 131A and 131B that are respectively analogous to the above-described steps 31A and 31B are situated at the bases of the longitudinal strips 130A and 130B.

Like the collar 18, the collar 118 may be made from two flat flanks that are welded together, or else in the form of a single piece that is obtained by molding, as shown in FIG. 6.

The extent to which the collar 118 projects beyond the opening 12A varies along the width of the collar between a minimum height h1 measured in the vicinity of the main fold line 117, and a maximum height h2 measured in the vicinity of the lateral end of the collar opposite from the main fold line, i.e. specifically the end where the first longitudinal end strip 130A and the sliding edge 132B are to be found.

As can be seen in FIG. 5, when the pouch is in the flat configuration, the free edge 118B of the collar opposite from the opening 12A forms a curve with a concave zone C1 that defines the free edge of the nose 118', at least in part. This curve also presents a convex zone C2 that extends between the concave zone C1 and the lateral end of the collar opposite from the main fold line 117.

This curve is substantially S-shaped, with a central portion in the form of a rising ramp connecting together the portions C1 and C2. Its respective terminal portions S1 and S2 are slightly rounded. This shape is particularly adapted for the pouch being used as a urinal for women. In order to use the pouch, it suffices to deform the collar so as to shape it into a channel, and to place the collar so that its lowest portion, corresponding to the portion S2, is situated against the posterior portion of the vulva.

In the variant of FIGS. 5 to 7, the collar also has spreader tabs. More precisely, the portion 118A of the collar that forms a segment of the collar inside the bag 12 presents spreader tabs 140A and 140B. These tabs are formed respectively as continuations of each of the two walls of the collar and they have respective free lateral ends 140'A and 140'B that are suitable for spreading apart from each other in the utilization configuration of the pouch in order to space apart the opposite faces of the flexible bag, as described in European patent application No. 0 847 742 and as can be understood from FIG. 6. These tabs are advantageously stiffened by ridges 141A and 141B, or the like.

The pouch of the invention advantageously includes means for holding the walls of the collar in their channel-forming shape.

Thus, the collar 118 has two holder tongues 150A and 150B that are carried respectively by the first wall 120A and by the second wall 120B. These tongues are situated towards the lateral ends of the wall that are remote from the main fold line 117 and they extend towards the free edge of the collar, i.e. away from the opening 12A of the pouch.

More precisely, for each wall 120A or 120B, the holder tongue 150A or 150B extends between the edge of the wall opposite from the main fold line 117 (which edge specifically carries the strip 130A or the sliding edge 132B) and a respective notch 152A or 152B. Each notch points longitudinally towards the opening 12A of the pouch going from the free edge 118B of the collar.

As can be seen in FIG. 7, the tongues 150A and 150B overlap when the pouch is in its utilization configuration, with the collar forming the channel. In order to hold the collar in its channel shape, it is then possible to take hold of the two overlapping tongues, pinching them together between two fingers. Furthermore, in order to stabilize the channel shape of the collar, it is possible to fold the tongues outwards, along a bend line 153, visible in FIG. 7.

Naturally, the holder tongues are entirely compatible with the variant embodiment of FIGS. 1 to 4.

FIGS. 5 to 7 also show other means for holding the walls of the collar in their channel-forming configuration. The second portion of the longitudinal strip 130B carries an outwardly-projecting stud 154B, while the first longitudinal strip portion 130A presents a hole 154A that is to receive the stud when the collar is shaped into a channel, in order to hold the collar in this shape.

In general manner, the stud and the hole are situated respectively in two portions of the collar that overlap when the walls of the collar are in their channel shape, these two portions preferably being remote from the main fold line. Thus, when present, these two portions may be the two longitudinal strips, as shown.

Provision may also be made for the stud to cooperate with the opening by clipping or snap-fastening, or by means of any appropriate retaining system. For example, the stud could have a retaining head and the opening could have a keyhole shape, with a wide portion for insertion and a narrow retaining portion.

The holder means, which comprise the above-described tongues, and also the holder means comprising the stud and the opening, may be combined, as shown in FIGS. 5 to 7, or else only one or the other of these means may be provided.

In general manner, any means may be provided for holding the collar in its channel shape, whether they be means as described above or other means, e.g. making use of adhesive, or the like.

The invention claimed is:

1. A pouch comprising:
a flexible bag having an opening whose edge is fastened to two opposite walls of a reinforcing collar projecting out from the bag, the pouch being able to adopt a flat configuration in which the collar is folded along a main fold line connecting together the two opposite walls so that said walls are situated one against the other, and a utilization configuration in which the two opposite walls form a channel holding the opening open,
wherein the main fold line presents an end portion opposite from the opening that projects laterally outwards, such that in the utilization configuration, the collar presents a nose defined by said end portion,
wherein the end portion projects laterally outwards when the pouch is in the flat configuration and when the pouch is in the utilization configuration,
wherein the main fold line presents a concave side facing towards the outside of the collar, and
wherein each of the walls of the collar presents a secondary fold line that connects the main fold line to a free edge of the collar opposite from the opening, and that, in the utilization configuration, forms a boundary between the nose and a remaining portion of the collar.

2. A pouch according to claim 1, wherein the secondary fold lines of the two opposite walls are symmetrical relative to the main fold line.

3. A pouch according to claim 1, wherein the secondary fold lines of the two opposite walls are curved, with concave sides facing towards the main fold line.

4. A pouch according to claim 1, wherein, at a side opposite from the main fold line, the first wall of the collar presents a first longitudinal end strip; projecting laterally relative to the edge of the opening, and the second wall presents a sliding edge suitable for sliding against the inside face of said first longitudinal strip while the pouch is passing from the flat configuration to the utilization configuration.

5. A pouch according to claim 1, wherein the walls of the collar are to be held in the form of the channel.

6. A pouch according to claim 1, wherein the collar presents holder tongues carried respectively by the first wall and the second wall of the two opposite walls of the collar, on the side opposite from the opening of the pouch and in a zone that is remote from the main fold line, the holder tongues overlapping at least in part in the utilization configuration.

7. A pouch according to claim 6, wherein, for each of the first wall and the second wall, the holder tongue extends between an edge of the wall opposite from the main fold line and a notch that extends substantially longitudinally towards the opening from a free edge of the collar.

8. A pouch according to claim 1, wherein two portions of the collar, that are to move into overlap when the two opposite walls of the collar form the channel, present respectively a hole and a lug that is suitable for being engaged in said hole.

9. A pouch according to claim 8, wherein the two portions that are to move into overlap are situated in respective zones of the first wall and second wall of the two opposite walls of the collar that are remote from the main fold line.

10. A pouch according to claim 1, wherein the extent to which the collar projects from the opening varies across the width of the collar, between a minimum height measured in the vicinity of the main fold line and a maximum height measured in the vicinity of the lateral end of the collar opposite from the main fold line.

11. A pouch according to claim 10, wherein, in the flat configuration of the pouch, a free edge of the collar opposite from the opening forms a curve having a concave zone that defines at least a portion of a free edge of the nose.

12. A pouch according to claim 11, wherein the curve has a convex zone that extends between said concave zone and the lateral end of the collar that is opposite from the main fold line.

13. A pouch comprising a flexible bag having an opening whose edge is fastened to two opposite walls of a reinforcing collar projecting out from the bag, the pouch being able to adopt a flat configuration in which the collar is folded along a main fold line connecting together its walls so that said walls are situated one against the other, and a utilization configuration in which the walls form a channel holding the opening open, wherein the main fold line presents an end portion opposite from the opening that projects laterally outwards, such that in the utilization configuration, the collar presents a nose defined by said end portion,     wherein the end portion projects laterally outwards when the pouch is in its flat configuration and when the pouch is in its utilization configuration, wherein the main fold line presents a concave side facing towards the outside of the collar, and     wherein the collar presents two holder tongues carried respectively by the first and second walls of the collar, on the side opposite from the opening of the pouch and in a zone that is remote from the main fold line, the holder tongues overlapping at least in part in the utilization configuration.

14. A pouch according to claim 13, wherein, for each wall, the holder tongue extends between an edge of the wall opposite from the main fold line and a notch that extends substantially longitudinally towards the opening from the free edge of the collar.

* * * * *